United States Patent [19]

Morrison et al.

[11] Patent Number: 4,595,779

[45] Date of Patent: Jun. 17, 1986

[54] STABLE LITHIUM DIISOPROPYLAMIDE AND METHOD OF PREPARATION

[75] Inventors: Robert C. Morrison, Gastonia; Randy W. Hall, Kings Mountain; Terry L. Rathman, Gastonia, all of N.C.

[73] Assignee: Lithium Corporation of America, Inc., Bessemer, N.C.

[21] Appl. No.: 685,318

[22] Filed: Dec. 24, 1984

[51] Int. Cl.$^4$ .................... C07C 85/26; C07C 87/123
[52] U.S. Cl. ......................................... 564/2; 564/463
[58] Field of Search ................................. 564/2, 463

[56] References Cited

U.S. PATENT DOCUMENTS

| | | | |
|---|---|---|---|
| 3,197,516 | 7/1965 | Esmay et al. | 260/665 |
| 3,388,178 | 6/1968 | Kamienski | 260/665 |
| 3,446,860 | 5/1969 | Beumel | 260/665 |
| 3,694,516 | 9/1972 | Morrison | 260/665 R |
| 4,006,187 | 2/1977 | Kamienski | 260/557 |
| 4,399,078 | 8/1983 | Morrison | 260/665 R |

OTHER PUBLICATIONS

H. Normant et al. C.A., vol. 70; 105864h (1969).
H. Normant et al. C.A. 1964; 18549f.
Gilman et al., J. Organometal. Chem., 4 (1965) 483–487.
Gilman and Gaj, J. Am. Chem. Soc. 22, 1165 (1957).
Honeycutt, J. Organometal. Chem., 29 (1971) 1–5.
Bates et al., J. Org. Chem., vol. 37, No. 4, (1972) 560–563.
M. T. Reetz and W. F. Maier, Liebigs Annalen der Chemie, vol. 10 (1980) pp. 1471–1473.
F. Gaudemar-Bardone et al., Jun. 1979, pp. 463–465.
R. A. Ellison et al., J. Organometallic Chemistry, 36, (1972) pp. 209–213.

*Primary Examiner*—Charles F. Warren
*Assistant Examiner*—Carolyn S. Greason
*Attorney, Agent, or Firm*—Bell, Seltzer, Park & Gibson

[57] ABSTRACT

The present invention provides a nonpyrophoric and thermally stable form of lithium diisopropylamide which is useful as a reagent in the preparation of pharmaceuticals and specialty chemicals. The preferred composition includes lithium diisopropylamide, a limited amount of tetrahydrofuran in an amount not exceeding one mole per mole of lithium diisopropylamide, and at least one $C_2$ to $C_{18}$ amine.

22 Claims, No Drawings

STABLE LITHIUM DIISOPROPYLAMIDE AND METHOD OF PREPARATION

BACKGROUND OF THE INVENTION

This invention relates to a stable lithium diisopropylamide (LDA) composition, and a method of its preparation.

Lithium diisopropylamide (LDA) is widely used as a reagent in the preparation of pharmaceuticals and specialty chemicals. LDA has a low solubility and irreversibly precipitates in hydrocarbon solvents. Consequently, LDA is not commercially available in solution form. The only commercially available LDA has been as a pyrophoric solid or slurry in hydrocarbon, and this has been available only in low volumes. The safety hazard in the shipment and handling of the pyrophoric LDA solid or slurry, as well as the difficulty in using these forms of LDA in reactions, severely limit the usefulness of these LDA forms in commercial applications.

Users of LDA generally prefer an LDA solution. Although LDA is soluble in ethers, it is quite unstable in this medium and quickly decomposes at room temperatures. Therefore, large volume users of LDA must synthesize their own LDA as it is needed, typically by reacting n-butyllithium with diisopropylamide in cold tetrahydrofuran (THF). This reaction is fairly easy to carry out, but may present safety hazards for those users unfamiliar in the handling of pyrophoric n-butyllithium.

Accordingly, the need exists for a stable and nonpyrophoric form of lithium diisopropylamide which could be produced and shipped in quantity and which presents fewer handling problems than the currently available forms of lithium diisopropylamide.

SUMMARY OF THE INVENTION

In accordance with the present invention, it has been found that a composition comprising lithium diisopropylamide and a limited amount of tetrahydrofuran, forms a lithium diisopropylamide composition which is thermally stable at mild temperatures for several months. Furthermore, the composition is nonpyrophoric and thus fewer precautions are required to ensure safe shipping and handling.

Tetrahydrofuran (THF) is the preferred liquid ether for use in the present invention, since LDA is quite soluble in THF. However, as earlier noted, the currently available forms of LDA are unstable in the presence of THF.

It has been found that by limiting the amount of THF to no more than about 1 mole of THF for each mole of LDA present, an LDA/THF composition is obtained which exhibits enhanced thermal stability. Preferably, the mole ratio of THF to LDA is within the range of 0.5:1 to 1:1, and most desirably within the range of 0.8:1 to 1:1.

Additionally, it has been surprisingly discovered that the presence in the LDA composition of small amounts of excess diisopropylamine, one of the reactants in the preparation of the LDA, and/or the presence of other amines, such as non-metalable triethylamine (TEA) for example, has a significant stabilizing effect on the decomposition of the LDA.

Thus, in accordance with one broad aspect of the present invention, there is provided a stable, nonpyrophoric form of lithium diisopropylamide comprising lithium diisopropylamide, and tetrahydrofuran in an amount not exceeding about one mole of tetrahydrofuran per mole of lithium diisopropylamide. For added stability, the composition may also include at least one $C_2$ to $C_{18}$ amine.

In its preferred and more limited aspects, the present invention provides a stable, nonpyrophoric lithium diisopropylamide solution which comprises a 1 to 3 molar solution of lithium diisopropylamide in a mixture of tetrahydrofuran, at least one amine selected from the group consisting of diisopropylamine and triethylamine, and an inert liquid hydrocarbon cosolvent, the tetrahydrofuran being present in an amount not exceeding about 1 mole of tetrahydrofuran per mole of lithium diisopropylamide.

While the soluble, stable LDA composition of the present invention can be produced by any of several different methods, including the conventional method involving the reaction of n-butyllithium with diisopropylamine, as well as by reacting other organolithiums and organodilithiums, such as methyllithium, ethyllithium, phenyllithium, cyclohexyllithium, dilithiobutane for example, the preferred method of preparation in accordance with the present invention involves the preparation of lithium diisopropylamide directly from lithium metal. This approach has very significant economic advantage over the traditional method of preparation, since one mole of lithium metal will produce one mole of LDA, while two moles of lithium metal are required when producing LDA from an alkyllithium compound.

In accordance with the preferred method of the present invention, the lithium diisopropylamide is produced directly from lithium metal with the use of an electron carrier such as styrene or isoprene. The reaction is carried out in tetrahydrofuran (THF), with the amount of the THF being limited to no more than two moles per mole of electron carrier. Limiting the amount of THF results in a stable product, as earlier noted, and also advantageously avoids sticking together of the lithium metal during the reaction. An inert liquid hydrocarbon cosolvent may also be employed to adjust the final LDA concentration as desired. The stable LDA composition produced by this method will also include as a part of the hydrocarbon cosolvent system, the reduced electron carrier, e.g. ethylbenzene (b.p=136° C.) where styrene was used as the electron carrier and 2-methyl-2-butene (b.p=36° C.) where isoprene was used. Since the boiling points of these two byproducts differ widely, the particular electron carrier which is used may be selected to facilitate recovery of the user's end product from the reduced electron carrier. Thus, for example, where the end product is a liquid, if the user is preparing a high boiling compound, an LDA solution containing the low boiling 2-methyl-2-butene would be selected, whereas the choice for a low boiling compound would be an LDA solution containing ethylbenzene. For those instances where the butene or ethylbenzene are not suitable, other electron carriers may be used, such as butadiene, divinylbenzene, and naphthalene, for example depending upon the method of separation to be employed.

In accordance with an alternative method in accordance with the present invention, LDA was also prepared for the first time in a non-ethereal solvent. In accordance with this aspect of the present invention, LDA is prepared directly from lithium metal and an electron carrier such as styrene or isoprene, in the presence of diisopropylamine in a hydrocarbon solvent, producing a stable but relatively insoluble mass which may be later rendered soluble if desired by addition of tetrahydrofuran.

DETAILED DESCRIPTION OF THE INVENTION

The present invention will be understood more fully from the description which follows, and from the accompanying examples, in which particular embodiments of the invention are shown. It is to be understood at the outset, however, that persons of skill in the appropriate arts may modify the invention here described while still achieving the favorable results of this inven-

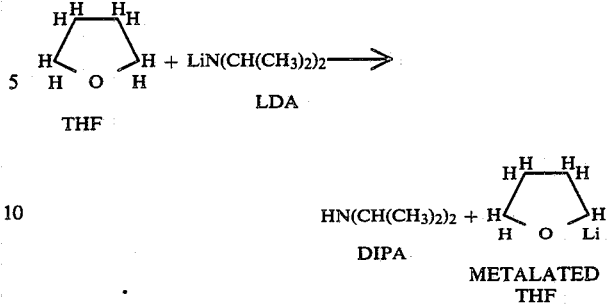

TABLE I

| Sample No. | LDA Route | Conc. (N.) | THF/LDA (Mole Ratio) | \multicolumn{4}{c}{LDA % Loss/Day at Various °C.} | Stabilizer[1] | (Mole %) |
|---|---|---|---|---|---|---|---|---|---|
| | | | | 0° C. | 20.5 ± 2.5° C. | 27.5 ± 7.5° C. | 40° C. | | |
| A | NBL[6] | 1.50 | 1.00 | 0[4] | 0.06[3] | 0.20 | | TEA | (5.0) |
| B | Styrene | 1.50 | 0.92 | 0[4] | 0[3] | 0.16 | | DIPA | (14.2) |
| C | Styrene | 0.75 | 6.40 | | 15.80 | | | DIPA | (14.2) |
| D | NBL[6] | 1.50 | 2.00 | | 0.49 | | | DIPA | (7.2) |
| E | Styrene | 2.92 | 1.13 | 0.05 | 0.06[3] | 0.32 | | DIPA | (18.0) |
| F | Styrene | 1.43 | 0.54 | (5) | 0[5] | 0.19 | | DIPA | (4.0) |
| G | Styrene | 1.60 | 0.85 | (4) | | 0.39 | | None | (0) |
| H | Isoprene | 1.54 | 0.82 | (4) | | 0.20 | | DIPA | (7.0) |
| I | Styrene | 2.29 | 0.95 | (4) | | 0.13 | | DIPA | (10.6) |
| J | Isoprene | 2.39 | 0.90 | (4) | | 0.21 | | DIPA | (4.0) |
| K | NBL[6] | 1.50 | 2.00 | | 0.17 | | | TEA | (5.6) |
| L | NBL[6] | 1.50 | 3.20[2] | 0.18 | 2.9 | | | DIPA | (7.0) |
| M | Styrene | 2.76 | 0.87 | | | | 1.49 | DIPA | (0) |
| N | Styrene | 1.75 | 0.87 | | | | 1.32 | DIPA | (2.7) |
| O | Styrene | 2.76 | 0.89 | | | | 1.16 | DIPA | (5.4) |
| P | Styrene | 1.76 | 0.89 | | | | 0.81 | DIPA | (11.8) |
| Q | Styrene | 1.86 | 1.71[7] | 1.05 | | | 7.50 | DIPA | (27.0) |

[1]TEA = triethylamine; DIPA = diisopropylamine and is the amount used in excess.
[2]Used t-butylmethylether (TBME) instead of THF (TBME/LDA - 3.20)
[3]After 30 days sample slightly turbid.
[4]After 30 days sample clear yellow containing no pptn, thus no degradation.
[5]After 30 days LDA precipitated from solution.
[6]NBL = n-butyllithium
[7]used ethyl ether instead of THF (Et₂O/LDA = 1.71)

tion. Accordingly, the description and examples which follow are to be understood as being a broad teaching disclosure directed to persons of skill in the appropriate arts, and are not to be understood as limiting upon the present invention.

I. Thermal Stability of LDA Solutions

Tests were conducted to determine the thermal stability of various LDA solutions as a function of several variables, and the results are summarized in Table 1 below. These tests illustrate how LDA compositions in accordance with the present invention exhibit superior thermal stability as compared to LDA compositions not in accordance with the invention. The LDA solutions were prepared either from lithium metal in the presence of THF and diisopropylamine through the use of a styrene or isoprene electron carrier in accordance with the procedures described in Example 1 below, or by the conventional route by reacting n-butyllithium (NBL) with diisopropylamine in THF. The decomposition of the LDA was determined from gas chromatography methods based upon the free diisopropylamine (DIPA) resulting from the metalation of tetrahydrofuran by lithium diisopropylamide using active (non-hydrolized) injection techniques. The decomposition of LDA is understood to occur as follows:

The above table shows that at even relatively mild temperatures (20.5° C.±2.5° C.) LDA solutions containing more than one mole equivalent of THF decompose rapidly, liberating free DIPA via metalation of uncomplexed THF. For example, LDA solutions containing 2 and 6.4 mole equivilants THF/LDA (Samples D and C), lose 15% and 100% activity after 30 days and 7 days, respectively. Conversely, LDA solutions containing 1 or less mole equivalents THF/LDA were found to be thermally stable.

At elevated temperatures (27.5° C.±7.5° C.) all LDA solutions tested degraded. LDA solutions with limited THF (THF/LDA=0.5 to 1) decomposed slightly (6% loss in 30 days) while an LDA solution containing only a slight excess of THF (THF/LDA=1.13) depicted an accelerated rate of decomposition (10% loss in 30 days).

Refrigerated samples (0° C.) containing 1 equivalent of THF or less remained clear yellow and stable. However, a small amount of decomposition (1.5% after 30 days) was noted for a refrigerated sample (see Sample E above) which contained a slight excess of THF (THF/LDA=1.13). Finally, an LDA sample (F above) containing 0.54 mole equivalents THF deposited a white crystalline precipitate on the walls and bottom of the sample bottle after 50 days at room temperature and 0° C. Additional THF redissolved the precipitate, which was identified as LDA. Samples containing 0.82 to 0.95 mole equivalents THF/LDA remained clear (no pptn.) at 0° C. for at least 90 days indicating no solubility or stability problem (see samples B, G, H, I and J).

In summary, the use of excess THF (THF/LDA>1) results in LDA solutions which rapidly decompose at room temperature. LDA solutions containing THF in an amount below the preferred minimum level (THF/LDA=0.5) slowly precipitate product. The preferred operating range to produce a thermally stable and soluble LDA product is from 0.5 to 1, and most desirably from 0.8 to 1.

During the course of thermal stability studies it was surprising to learn that the presence of small amounts of excess diisopropylamine (DIPA) or even non-metalable triethylamine (TEA) had a stabilizing effect on the decomposition of solutions of LDA in THF/cyclohexane. The rate of decomposition of an LDA solution containing no stabilizer (Sample G) was twice (11.7% loss/mo.) that of comparable LDA solutions (6% loss/mo.) containing excess DIPA or TEA (4 and 5 mole %—Sample F, J and A). LDA solutions containing more stabilizer (10+%) degraded even less (4% loss/mo. Sample I and B). At 40° C. all LDA samples tested degraded. However, with increasing stabilizer the degradation rate/day significantly decreased from 1.49 to 0.81%/day (samples M, N, O and P). Interestingly, an LDA solution containing 13 mole % excess THF and 18 mole % stabilizer (see above Table Sample E) thermally degraded at all three test temperatures. Also, LDA solutions (Sample D and K) containing 100% excess THF degraded at significantly different rates (0.49 and 0.17%/day) due to the use of different stabilizers, indicating that TEA may be superior to excess DIPA.

Thus, it was apparent from the above data that the presence of excess DIPA plays an important role as a stabilizer in the preparation of an LDA solution, and the preferred DIPA level appears to be about 4 to 100 mole percent, with the optimum level about 10 mole percent.

Thermal stability of LDA solutions of various compositions were tested under simulated spring and summer plant temperatures (18° to 35° C.) and also under refrigerated conditions (0° C.). The data is presented in the summary table above. At 0° C. LDA solutions, ideal in terms of THF and stabilizer (discussed above) remained clear light yellow with no precipitation and stable for three months (see Samples A, B, G, H, and I). However, samples with excess ether (THF or t-butylmethylether(TBME)) underwent some thermal decomposition at 0° C. depending on how much excess ether was present (see Sample E and L). At the intermediate temperature level (20.5°±2.5° C.) an ideal LDA sample (Sample B) was thermally stable (no increase in free DIPA), but deepened in color (lt. orange) and became quite hazy. Another sample (Sample F) showed no decomposition at 20.5°±2.5° C., but was metastable in that precipitation of LDA occurred because of insufficient THF. Other samples decomposed, deepened in color and became hazy with solids to varying extents, depending on the amount of excess Lewis base (Samples C, E, D, K, and L). At elevated temperature (27.5°±7.5° C.) all samples degraded, deepened in color and generated insoluble particulate matter, again, depending upon the major variables (see summary table above and FIGS. I, II and III). The most stable LDA solution (0.13% loss/day) at 27.5°±7.5° (Sample I) contained 10.6 mole % stabilizer and less than 1 equivalent THF (THF/LDA=0.95).

In summary, all LDA solutions degrade and produce insoluble degradation products at elevated temperatures (27.5°±7.5° C. and 40° C.). At intermediate temperatures (20.5°±2.5° C.) LDA samples containing optimum amounts of THF and stabilizer do not decompose according to GLC methods, but do deepen in color and form slight haziness. At 0° C. LDA solution containing slightly less than 1 equivalent of ether are stable and remain clear yellow.

The thermal stability of the LDA-THF composition appears to be not significantly affected by the LDA concentration, and 1:1 LDA-THF solutions as high as 3.6M may be prepared directly from lithium metal by the electron carrier route in the absence of hydrocarbon cosolvent. However, at concentrations greater than 2.3M LDA, the composition will precipitate at lower temperatures, but can be redissolved at room temperature. While the solid or slurry form may be useful in certain applications, the solution form is most conveniently handled. Accordingly, to avoid precipitation during storage and shipment under refrigeration where the solution form is required, it is desirable that the concentration be no greater than 2.3M. A preferred range of concentrations for practical commercial quantities of the LDA solution is from about 1 to about 2.3M.

B. Preparation of Stable LDA Solutions

The preferred method of preparation in accordance with the present invention involves reacting lithium metal particles in an ether medium, preferably tetrahydrofuran, wherein the amount of ether does not exceed about 2 moles of ether per mole of electron carrier, with an electron carrier and with slightly more than 2 moles of diisopropylamine per mole of electron carrier to thereby produce a soluble, stable lithium diisopropylamide composition. In this reaction, the electron carrier is the limiting reagent. The electron carrier is characterized by its ability to readily receive an electron from the lithium and form a radical anion. Conjugated unsaturated hydrocarbons are noted for this ability, as shown by Ziegler et al., Liebigs Annalen der Chemie, 511, 64 (1934), and particularly preferred for use as an electron carrier in the present invention are styrene and isoprene. Other suitable electron carriers may include butadiene, divinylbenzene and napthelene for example.

The production of lithium diisopropylamide directly from lithium metal through the use of an electron carrier, namely styrene, has been previously described, see M. T. Reetz and W. F. Maier, Liebigs Annalen der Chemie, 10, 1471 (1980). In this procedure, LDA was prepared by adding a styrene/ethyl ether feed to a refluxing slurry of granulated lithium and diisopropylamine in ethyl ether. The formation of LDA is promoted by styrene which functions as an electron carrier by accepting an electron from the metal to form a radical anion. The radical anion is rapidly quenched by diisopropylamine to form LDA and a neutrally charged radical. The electron carrier then receives a second electron from another lithium atom to form what is believed to be alpha-methylbenzyllithium which subsequently is quenched by diisopropylamine to form a second lithium diisopropylamide. However, the resulting LDA rapidly metalates the ethyl ether, forming the expected decomposition products ethylene and lithium ethoxide, as identified by NMR.

Having discovered in accordance with the present invention that enhanced stability is achieved by limiting the amount of THF, applicants repeated the Reetz et al procedure limiting the amount of ethyl ether to 1 mole equivalent per mole equivalent of LDA. However, it was found that the resulting composition is not sufficiently soluble to be of commercial value. The subsequent addition of ethyl ether to give a 1.7 ether to LDA ratio gave a soluble solution. However, the thermal stability of the resulting composition, even in the presence of a large excess of stabilizer (DIPA) was considerably less than the composition of this invention (see Table I, sample Q). It is surprising that this enhanced stability is achieved using THF, since it is well recognized that THF is a much more labile ether than ethyl ether.

In preparing the lithium diisopropylamide in accordance with the preferred method of this invention, it has been found that significant improvements in yield are achieved by combining the majority of the total THF requirement with the electron carrier feed. The reaction vessel thus contains only the diisopropylamine, the hydrocarbon solvent, the lithium metal, and the remaining balance of the THF requirement. For example, yields as high as 95% have been achieved by combining 90% of the total THF requirement with the electron carrier feed, and adding the THF and electron carrier (e.g. styrene or isoprene) dropwise to the reaction vessel. The addition of most of the required THF along with the electron carrier feed permits the formation of LDA in the absence of excess free THF, and thus limits the probability of metalation of the THF by in situ formed LDA.

It has also been found to be desirable to initially heat the reaction mixture to about 35° to 40° C. prior to addition of the electron carrier feed so as to accelerate initiation of the reaction. Once the reaction is initiated, it is sufficiently exothermic that cooling is generally required to maintain an optimum reaction temperature of about 30° to 45° C. The rate of dropwise addition of the THF in electron carrier mixture is limited by the efficiency in cooling the reaction vessel to maintain the desired reaction temperature. Excessive reaction temperatures are to be avoided, as this encourages the formation of side products resulting from metalation of THF, ethyl benzene and/or loss of LiH from various lithium species.

It has also been discovered in accordance with the present invention that it is possible to prepare LDA in the absence of an ether solvent. LDA has been prepared in the absence of THF by adding styrene dropwise to a stirred dispersion containing lithium sand in diisopropylamine and cyclohexane. The resulting product mass was very viscous, contained solids and appeared to be unfilterable. The addition of 100% excess DIPA failed to dissolve the product. However, the addition of one equivalent of THF dissolved the solids and thinned the product mass to a filterable solution. While the yield from this procedure is relatively low (65%), a significant yield improvement (86%) was observed upon repeating the described etherless preparation of LDA in the presence of about one equivalent triethylamine. The resulting composition was viscous, but again could be thinned by addition of THF. See Examples 6 and 16 below.

In the practice of the present invention, pure or essentially pure lithium metal or a commercial source of lithium metal is used. While lithium in the form of rod, shot and powder can be used, the preferred form of lithium metal for use in the present invention, for reasons of handling and good reactivity, is particulate lithium of a particle diameter of about 500 to about 5000 microns (about 12 to about 100 mesh) known as lithium sand. It has been found desirable to use at least a 10% excess of lithium for good yields.

The diisopropylamine (DIPA) and tetrahydrofuran (THF) and electron carriers (e.g. styrene and isoprene) are used as received from the supplier. Typically, these reagents are colorless liquids, 99+ percent pure. As much as a total of 0.165 percent water has been present in these materials without any noticeable adverse effects in the yields of LDA. It is also desirable to use a slight excess of diisopropylamine.

Other amines which may be useful in the composition as stabilizers include amines ranging from $C_2$ to $C_{18}$ such as diethylamine, ethylamine, di-n-propylamine, dibutylamines, diarylamines, dihexylamines, dicyclohexylamine, hexamethyldisilazane, butylamine, hexylamine and cyclic amines, such as derivatives of pyrrolidine and piperidine and even diamines such as tetramethylethylenediamine, and other tertiary amines such as tri-n-propylamine, tri-n-butylamine, tri-n-hexylamine.

The preferred cosolvent for use in the present invention is cyclohexane. Other cosolvents which may be used to customize the product for particular applications include toluene, xylene, n-heptane, n-hexane, benzene, and cyclic or straight or branched chain $C_5$ to $C_{10}$ hydrocarbons such as pentanes, hexanes, and heptanes, or mixtures of paraffinic hydrocarbons such as petroleum ether.

EXAMPLE 1

Preparation of LDA Complex

An oven dry 500 ml three-neck, round bottomed flask equipped with a pressure equalizing dropping funnel, mechanical stirrer, Y-tube, thermometer well and cold finger condenser was assembled while hot and purged with argon until cool. The reaction vessel was charged with 0.70 mole of lithium metal, 0.65 mole diisopropylamine and 0.056 mole dry THF. Target molarity of the LDA solution may be controlled by prereaction addition of cyclohexane. For example, add 103 ml of cyclohexane for a theoretical 2.3M solution or 251 ml of cyclohexane for a 1.5M solution. Next, the reaction mixture was heated to about 35° C. using a hot air gun or heating mantle, followed by dropwise addition of a solution of 0.32 mole styrene in 0.52 mole dry THF over a thirty minute period while maintaining a reaction temperature of 35°–40° C. by cooling in a dry ice/hexane bath. The reaction was complete in about three hours. The resulting dark grey mixture was filtered to remove a small excess of lithium metal and other insolubles (e.g. LiOH), and yielded a pale yellow to amber colored solution of LDA.

EXAMPLES 2–16

Preparation of LDA from lithium metal

Samples of LDA were prepared using a procedure similar to that described in Example 1, and employing varying amounts of lithium, DIPA, THF, and either styrene or isoprene as the electron donor, all as set forth in Table II below. The actual concentrations are shown in the table, and the actual yield as determined by the amount of ethyl benzene or 2-methyl-2-butene generated. Yields were also confirmed by wet analysis (total and active lithium).

TABLE II

| | LDA PREPARED USING LITHIUM METAL | | | | | |
|---|---|---|---|---|---|---|
| | Mole Ratio of Materials | | | | Avg Temp | |
| Example | Li[I] | DIPA | Styrene/Isoprene | THF | (°C.) | Yield %[H] |
| 2 | 1.00 | 1.00 | 0.500* | — | 2.53 | 37 | 86[K] |
| 3 | 1.20 | 1.00* | 0.539 | — | 2.53 | 35 | 85[K] |
| 4 | 1.00* | 1.05 | 0.504 | — | 1.01 | 36 | 93 |
| 5 | 1.10 | 1.00* | 0.527 | — | 0.523 | 32 | 93 |
| 6 | 1.00* | 1.29 | 0.532 | — | 0[A] | 38[L] | 65 |
| 7 | 1.62 | 1.00* | 0.513 | — | 0.105[B] | 37[L] | 89 |
| 8 | 1.18 | 1.00*[J] | 0.517 | — | 0.875[C] | 35[D] | 98 |
| 9 | 1.14 | 1.00*[J] | — | 0.528 | 0.869[C] | 36[D] | 100 |
| 10 | 1.10 | 1.02[J] | 0.500* | — | 0.887[C] | 38[D] | 100 |
| 11 | 1.12 | 1.04[J] | — | 0.500* | 0.907[C] | 37[D] | 99 |
| 12 | 1.12 | 1.00 | 0.500* | — | 0.874[C] | 35[D] | 95 |
| 13[E] | 1.12 | 1.00 | 0.500* | — | 0.874[C] | 35[D] | 95 |
| 14 | 1.15 | 1.03 | 0.500* | — | 0.904[C] | 35[D] | 94 |
| 15[F] | 1.15 | 1.03 | 0.500* | — | 0.904[C] | 35[D] | 94 |
| 16 | 1.24 | 1.00* | 0.528 | — | 0[G] | 35[D] | 86 |

[A]LDA prepared as very viscous mixture; 0.094m THF was added to solubilize.
[B]Product because very viscous near end of reaction, so added 0.35 eq THF to thin enough to filter.
[C]Approx. 10% of THF in the reaction mixture; the other 90% added with electron carrier feed.
[D]Heated reaction mixture to about 35° C. before beginning electron carrier feed.
[E]Prepared by diluting Example 12 with cyclohexane.
[F]Prepared by diluting Example 14 with cyclohexane.
[G]No THF in the reaction step (used 1.06 eq triethylamine (TEA) as a substitute); however, the final reaction mixture was very viscous with LDA precipitating, so added 0.45 mole eq THF to solubilize.
[H]Yield based on amount of ethylbenzene or 2-methyl-2-butene generated.
[I]Lithium metal sand.
[J]DIPA contained 0.165% H₂O.
[K]Yield based on Watson-Eastham (active base) titration of the LDA solution.
[L]The reaction mixture required heating to approx. 35° C. before the exothermic reaction would begin.
*Limiting reagent The above examples present several experiments showing various preparations of LDA using styrene or isoprene as an electron carrier in ether or etherless solvent and hydrocarbon cosolvent. Yield optimization was observed by limiting the amount of THF. For instance when the mole ratio of THF was greater than one (examples 2 and 3) the yields were 86 and 85%, respectively. When no THF (example 6) was employed the yield dropped to 65%; however, this yield was improved to 86% by using triethylamine as a cosolvent in example 16. A noticeable yield improvement to 93% was observed in examples 4 and 5 where the mole ratio of THF was limited to 1 and 0.5 respectively. Still further yield improvement was achieved by combining the THF with the electron carrier feed. This optimization in procedure is clearly shown by examples 8 through 15 where the yields are greater than 94%.

That which is claimed is:

1. A stable, nonpyrophoric form of lithium diisopropylamide, comprising lithium diisopropylamide in the presence of tetrahydrofuran in an amount not exceeding about 1 mole of tetrahydrofuran per mole of lithium diisopropylamide.

2. A composition according to claim 1 additionally comprising at least one C₂ to C₁₈ amine stabilizer.

3. A composition according to claim 2 wherein said at least one amine is selected from the group consisting of diisopropylamine and triethylamine.

4. A composition according to claim 2 wherein said at least one amine is present in an amount of about 4 to about 100 mole percent.

5. A composition according to claim 1 additionally comprising an inert liquid hydrocarbon cosolvent and wherein the lithium diisopropylamide is present in the composition at a concentration of up to about 2.5 molar.

6. A stable, soluble nonpyrophoric form of lithium diisopropylamide comprising a 1 to 3 molar solution of lithium diisopropylamide in a mixture of tetrahydrofuran, at least one amine selected from the group consisting of diisopropylamine and triethylamine, and an inert liquid hydrocarbon cosolvent, the tetrahydrofuran being present in an amount not exceeding about 1 mole of tetrahydrofuran per mole of lithium diisopropylamide.

7. A composition according to claim 6 wherein the inert liquid hydrocarbon cosolvent includes ethylbenzene or 2-methyl-2-butene.

8. A composition according to claim 6 wherein said at least one amine is present at a concentration of 4 to 100 mole percent.

9. A stable, soluble nonpyrophoric form of lithium diisopropylamide comprising a 1 to 3 molar solution of lithium diisopropylamide in a mixture of tetrahydrofuran, diisopropylamine and an inert liquid hydrocarbon cosolvent, the amount of said tetrahydrofuran being from 0.8 to 1 mole of tetrahydrofuran per mole of lithium diisopropylamide, and said diisopropylamine being present at a concentration of about 4 to 100 mole percent.

10. A method of preparing a stable, nonpyrophoric lithium diisopropylamide composition comprising
    providing a mixture of lithium metal in diisopropylamine; and
    slowly adding to the mixture a feed solution containing an electron carrier while maintaining the mixture at a temperature of 30 to 45 degrees C. to thereby react the lithium metal and diisopropylamine and produce lithium diisopropylamide; and wherein said feed solution includes from 1 to 2 moles of tetrahydrofuran per mole of electron carrier.

11. A method according to claim 10 wherein said lithium metal and diisopropylamine mixture also includes tetrahydrofuran, and wherein the total of the tetrahydrofuran in said mixture and in said feed solution does not exceed two moles per mole of electron carrier.

12. A method according to claim 10 wherein said mixture also includes an inert liquid hydrocarbon cosolvent, and the thus formed lithium diisopropylamide is in solution.

13. A method according to claim 10 wherein said mixture contains an excess of lithium metal.

14. A method according to claim 10 wherein said lithium metal comprises lithium sand.

15. A method according to claim 10 wherein said mixture also contains an excess of diisopropylamine.

16. A method according to claim 10 wherein said mixture also includes triethylamine.

17. A method of preparing a stable, nonpyrophoric solution of lithium diisopropylamide comprising
providing a mixture of lithium metal in a solution of diisopropylamine, an inert liquid hydrocarbon solvent, and up to about one mole of tetrahydrofuran per mole of electron carrier;
slowly adding to said mixture a feed solution comprising an electron carrier selected from the group consisting of styrene and isoprene, and tetrahydrofuran, the amount of tetrahydrofuran not exceeding about one mole per mole of electron carrier, and wherein the total tetrahydrofuran in said mixture and in said feed solution is from one to two moles per mole of electron carrier; and
cooling the reaction mixture as the feed solution is added to maintain the temperature of the reaction mixture at from 30 to 45 degrees C. to thereby react the lithium metal and diisopropylamide and produce a solution of lithium diisopropylamide.

18. A method according to claim 17 wherein the feed solution contains about 1.8 moles of tetrahydrofuran per mole of electron carrier.

19. A method of preparing a stable, nonpyrophoric solution of lithium diisopropylamide comprising
providing a mixture of lithium metal in an etherless solution comprising diisopropylamine and an inert liquid hydrocarbon cosolvent;
slowly adding to the mixture an electron carrier selected from the group consisting of styrene and isoprene while maintaining the reaction at a temperature of 30 to 45 degrees C. to thereby react the lithium metal and diisopropylamine and produce a viscous, relatively insoluble mass containing lithium diisopropylamide; and
adding to the viscous, insoluble mass tetrahydrofuran in an amount not exceeding one mole per mole of lithium diisopropylamide to thereby solubilize the lithium diisopropylamide.

20. A method according to claim 19 wherein said mixture also includes triethylamine.

21. A method according to claim 19 wherein said mixture includes an excess of diisopropylamine.

22. A stable, nonpyrophoric form of lithium diisopropylamide, comprising lithium diisopropylamide in solution in the presence of tetrahydrofuran, wherein the mole ratio of tetrahydrofuran to lithium diisopropylamide is from 0.5:1 to 1.1.

* * * * *